(12) United States Patent
Nara et al.

(10) Patent No.: US 9,896,402 B2
(45) Date of Patent: Feb. 20, 2018

(54) METHOD FOR PREVENTING DECREASE IN OPTICAL PURITY

(75) Inventors: Hideki Nara, Fujisawa (JP); Yoshiki Hasegawa, Iwata (JP)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 255 days.

(21) Appl. No.: 14/355,895

(22) PCT Filed: Nov. 4, 2011

(86) PCT No.: PCT/JP2011/075491
§ 371 (c)(1),
(2), (4) Date: May 2, 2014

(87) PCT Pub. No.: WO2013/065189
PCT Pub. Date: May 10, 2013

(65) Prior Publication Data
US 2014/0296582 A1    Oct. 2, 2014

(51) Int. Cl.
| C07C 29/94 | (2006.01) |
| C07C 29/74 | (2006.01) |
| C07B 53/00 | (2006.01) |
| C07C 253/32 | (2006.01) |

(52) U.S. Cl.
CPC .............. *C07C 29/94* (2013.01); *C07B 53/00* (2013.01); *C07C 29/74* (2013.01); *C07C 253/32* (2013.01)

(58) Field of Classification Search
CPC ................................ C07C 29/74; C07C 29/94
USPC ....................................................... 568/810
See application file for complete search history.

(56) References Cited

U.S. PATENT DOCUMENTS

| 5,648,012 | A | 7/1997 | Higashibeppu et al. |
| 6,887,999 | B1 | 5/2005 | Likhotvorik |
| 2003/0004362 | A1 | 1/2003 | Tada et al. |
| 2007/0149831 | A1 | 6/2007 | Amano et al. |
| 2008/0228012 | A1 | 9/2008 | Ino et al. |
| 2010/0041888 | A1 | 2/2010 | Grote et al. |
| 2010/0081818 | A1 | 4/2010 | Grote et al. |
| 2010/0113788 | A1 | 5/2010 | Grote et al. |
| 2010/0324338 | A1 | 12/2010 | Maeda et al. |

FOREIGN PATENT DOCUMENTS

| CN | 101058532 A | 10/2007 |
| JP | 9-124367 A | 5/1997 |
| JP | 2003-034665 A | 2/2003 |
| JP | 2009-001545 A | 1/2009 |
| JP | 2009-534472 A | 9/2009 |
| JP | 2012-082179 A | 4/2012 |
| WO | 2005/092830 A1 | 10/2005 |
| WO | 2010/140636 A1 | 12/2010 |

OTHER PUBLICATIONS

Scholl et al., Org. Lett. vol. 1, No. 6, 1999, p. 953-956.*
European Patent Office; Communication dated Jun. 1, 2015 in counterpart application No. 11875211.2.
"Yuki Kagoubutsu no Gousei (Synthetic method of Organic Compounds)", Jikken Kagaku Kouza (Experimental Chemistry Course), fifth edition, p. 122, vol. 19, Maruzen Publishing Co., Ltd.
Ryoji Noyori, "Homogeneous Asymmetric Hydrogenation", Asymmetric Catalysis in Organic Synthesis, pp. 16-94.
Kazuhiko Matsumura et al., "Asymmetric Transfer Hydrogenation of α, β-Acetylenic Ketones", J. Am. Chem. Soc., 1997, pp. 8738-8739, vol. 119.
Akio Fujii et al., "Ruthenium(II)-Catalyzed Asymmetric Transfer Hydrogenation of Ketones Using a Formic Acid—Triethylamine Mixture", J. Am. Chem. Soc., 1996, pp. 2521-2522, vol. 118.
Koichi Mikami et al., "Asymmetric Activation/Deactivation of Racemic Ru Catalysts for Highly Enantioselective Hydrogenation Irrespective of Ketonic Substrates: Molecular Design of Dimethylbinaphthylamine for Enantiomeric Catalysts Discrimination", Adv. Synth. Catal., 2003, pp. 246-254, vol. 345, No. 1 and 2.
Japanese Patent Office, Communication issued in counterpart JP 2010-231523 dated Apr. 21, 2014.

* cited by examiner

*Primary Examiner* — Yong Chu
(74) *Attorney, Agent, or Firm* — Sughrue Mion, PLLC

(57) ABSTRACT

The present invention provides a method for producing a reduction reaction product, wherein recovery of the reaction solvent and/or distillation is carried out after adding a nitrogen-containing compound into a reaction liquid of a reduction reaction that has been conducted using a transition metal complex. The present invention is capable of suppressing decrease in the optical purity of the reduction reaction product due to the transition metal complex used as a catalyst.

5 Claims, No Drawings

METHOD FOR PREVENTING DECREASE IN OPTICAL PURITY

CROSS REFERENCE TO RELATED APPLICATIONS

This application is a National Stage of International Application No. PCT/JP2011/075491 filed Nov. 4, 2011, the contents of all of which are incorporated herein by reference in their entirety.

TECHNICAL FIELD

The present invention relates to a method for deactivating a transition metal complex used as a catalyst for producing a reduction reaction product by a reduction reaction, without loss in optical purity of the target product.

BACKGROUND ART

Hydrogenation and hydrogen transfer reactions using transition metal complexes are important methods for producing optically active compounds. It is known that prochiral ketones are reacted in the presence of a transition metal catalyst by using a secondary alcohol, formic acid, hydrogen, or the like as a hydrogen source, in general.

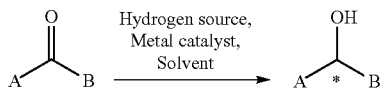

Since a transition metal catalyst having a reducing function also has an oxidizing function, oxidation of the produced secondary alcohol occurs in some cases, causing decrease in optical purity of the product.

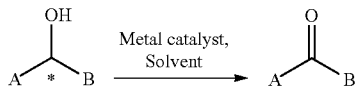

Since these reactions proceed under a neutral or basic condition, a method in which an acid such as hydrochloric acid is added or the like is employed for stopping these reactions.

SUMMARY OF INVENTION

Technical Problem

However, when the product is distilled in the presence of hydrochloric acid, the inside of a distillation apparatus is exposed to a high temperature and an acidic atmosphere, and hence the apparatus is more likely to be damaged. Hence, limitations are imposed on the reaction apparatus used and the operation method employed.

Solution to Problem

The present inventors have found that when a nitrogen-containing compound is added to a reaction solution of a reduction reaction, (i) the nitrogen-containing compound selectively reacts with a transition metal catalyst, and (ii) the reducing function and the oxidizing function of the transition metal complex are eliminated, so that the decrease in optical purity of a reduction reaction product is suppressed. This finding has led to the completion of the present invention.

The present invention includes the following contents [1] to [8].

[1] A method for producing a reduction reaction product, comprising:
adding a nitrogen-containing compound to a reaction solution in which a reduction reaction has been conducted by using a transition metal complex; and then
performing reaction solvent recovery and/or distillation.

[2] The production method according to the above-described [1], wherein the reduction reaction is an asymmetric hydrogenation, asymmetric hydrogen transfer, or ester reduction reaction.

[3] The production method according to the above-described [1] or [2], wherein the transition metal complex is a ruthenium complex, a rhodium complex, or an iridium complex.

[4] The production method according to the above-described [3], wherein one equivalent or more of the nitrogen-containing compound is added relative to the transition metal complex.

[5] The production method according to the above-described [4], wherein the number of nitrogen atoms in the nitrogen-containing compound is two or more.

[6] The production method according to the above-described [5], wherein the nitrogen-containing compound is an imidazole.

[7] The production method according to the above-described [1] to [6], wherein the addition of the nitrogen-containing compound is intended to suppress the decrease in optical purity of the reduction reaction product during the reaction solvent recovery and/or the distillation.

[8] The production method according to the above-described [7], wherein the addition of the nitrogen-containing compound results in a reaction of the nitrogen-containing compound with the transition metal complex to form a complex containing the nitrogen-containing compound, and thus suppresses the decrease in optical purity of the reduction reaction product.

Advantageous Effects of Invention

The present invention makes it possible to efficiently produce an optically active compound without causing decrease in optical purity during purification of the product conducted after a reduction reaction such as an asymmetric hydrogenation, asymmetric hydrogen transfer, or ester reduction reaction is conducted.

DESCRIPTION OF EMBODIMENTS

Hereinafter, the present invention will be described specifically.

Transition metals in the transition metal complex used in the present invention include metals of group 8 to 10 in the periodic table. Of these metals, rhodium, ruthenium, and iridium are preferable, and ruthenium is particularly preferable.

Preferred transition metal complexes include complexes in which a diamine, a diphosphine, a lower alkyl group (for example, a linear or branched alkyl groups having 1 to 10 carbon atoms, and specifically, a methyl group, an ethyl group, a n-propyl group, an isopropyl group, a n-butyl group, a s-butyl group, an isobutyl group, a t-butyl group, or the like; a linear or branched alkyl group having 1 to 6 carbon atoms is preferable), a substituted benzene, a halogen atom, pentamethylcylcopentadiene, or the like is coordinated as a ligand. The diamine and the diphosphine as the ligand is more preferably optically active.

Examples of the diamine include diamines represented by general formula (A):

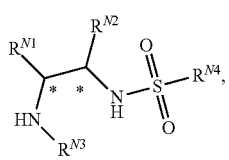

(A)

wherein * represents an asymmetric carbon atom; $R^{N1}$ and $R^{N2}$ each independently represent an optionally substituted $C_1$ to $C_{20}$ alkyl group, an optionally substituted $C_3$ to $C_8$ cycloalkyl group, an optionally substituted $C_7$ to $C_{20}$ aralkyl group, an optionally substituted $C_6$ to $C_{20}$ aryl group, or an optionally substituted $C_3$ to $C_{20}$ heterocyclic group, or $R^{N1}$ and $R^{N2}$ may together form an alkylene group or an alkylenedioxy group; $R^{N3}$ represents a hydrogen atom or an optionally substituted $C_1$ to $C_{20}$ alkyl group; and $R^{N4}$ represents an alkyl group having 1 to 10 carbon atoms, a halogenated alkyl group having 1 to 10 carbon atoms, or a $C_5$ to $C_{20}$ aryl group which may be substituted with an alkyl group (s) having 1 to 10 carbon atoms, a halogenated alkyl group (s) having 1 to 10 carbon atoms, or a halogen atom(s).

Substituents which may be possessed by the $C_1$ to $C_{20}$ alkyl group, the $C_3$ to $C_8$ cycloalkyl group, the $C_7$ to $C_{20}$ aralkyl group, the aryl group, or the heterocyclic group represented by $R^{N1}$ or $R^{N2}$ and substituents which may be possessed by the $C_1$ to $C_{20}$ alkyl group represented by $R^{N3}$ include methyl groups, ethyl groups, cyclopropyl groups, cyclobutyl groups, cyclopentyl groups, cyclohexyl groups, benzyl, 1-phenylethyl groups, phenyl groups, o-toluoyl groups, p-toluoyl groups, thienyl groups, furyl groups, pyridyl groups, piperidinyl groups, piperidino groups, and the like.

Specific examples of the optically active diamine include N-(p-toluenesulfonyl)-1,2-diphenylethylenediamine, N-methanesulfonyl-1,2-diphenylethylenediamine, N-trifluoromethanesulfonyl-1,2-diphenylethylenediamine, N-(p-fluorobenzenesulfonyl)-1,2-diphenylethylenediamine, N-pentafluorobenzenesulfonyl-1,2-diphenylethylenediamine, N-(p-methoxybenzenesulfonyl)-1,2-diphenylethylenediamine, N-(3,5-xylylsulfonyl)-1,2-diphenylethylenediamine, N-(2,4,6-trimethylbenzenesulfonyl)-1,2-diphenylethylenediamine, N-((1R)-camphorsulfonyl)-1,2-diphenylethylenediamine, N-(naphthylsulfonyl)-1,2-diphenylethylenediamine, N-(p-toluenesulfonyl)-1,2-cyclohexanediamine, N-methanesulfonyl-1,2-cyclohexanediamine, and N-trifluoromethanesulfonyl-1,2-cyclohexanediamine.

Examples of the diphosphine include diphosphines represented by general formula (B):

(B)

wherein $R^{P1}$, $R^{P2}$, $R^{P3}$, and $R^{P4}$ each independently represent an optionally substituted aryl group, an optionally substituted cycloalkyl group, or an optionally substituted alkyl group, or $R^{P1}$ and $R^{P2}$ and/or $R^{P3}$ and $R^{P4}$ may together form a ring(s); and Q represents an optionally substituted divalent arylene group or a ferrocenediyl group.

In the above formula, examples of the optionally substituted aryl group represented by $R^{P1}$, $R^{P2}$, $R^{P3}$ or $R^{P4}$ include aryl groups having 6 to 14 carbon atoms, and specifically include a phenyl group, a naphthyl group, an anthryl group, a phenanthryl group, a biphenyl group, and the like. These aryl groups may have one or two or more substituents, and the substituents include alkyl groups, alkoxy groups, aryl groups, heterocyclic groups, and the like.

The alkyl groups as the substituents in the aryl group include linear or branched alkyl groups having, for example, 1 to 15 carbon atoms, preferably 1 to 10 carbon atoms, and more preferably 1 to 6 carbon atoms, and specific examples thereof include methyl groups, ethyl groups, n-propyl groups, isopropyl groups, n-butyl groups, s-butyl groups, isobutyl groups, t-butyl groups, and the like.

The alkoxy groups as the substituents in the aryl group include linear or branched alkoxy groups having, for example, 1 to 6 carbon atoms, and specifically include methoxy groups, ethoxy groups, n-propoxy groups, isopropoxy groups, n-butoxy groups, s-butoxy groups, isobutoxy groups, t-butoxy groups, and the like.

The aryl groups as the substituents in the aryl group include aryl groups having, for example, 6 to 14 carbon atoms, and specifically include phenyl groups, naphthyl groups, anthryl groups, phenanthryl groups, biphenyl groups, and the like.

The heterocyclic groups as the substituents of the aryl group include aliphatic heterocyclic groups and aromatic heterocyclic groups. Examples of the aliphatic heterocyclic groups include 5 to 8-membered, preferably 5 or 6-membered monocyclic aliphatic heterocyclic groups having 2 to 14 carbon atoms and containing at least one, preferably 1 to 3 hetero atoms such as nitrogen atoms, oxygen atoms, and sulfur atoms; and polycyclic or condensed-cyclic aliphatic heterocyclic groups constituted of any of these monocyclic aliphatic heterocyclic groups. Specific examples of the aliphatic heterocyclic groups include 2-oxopyrrolidyl groups, piperidino groups, piperazinyl groups, morpholino groups, tetrahydrofuryl groups, tetrahydropyranyl groups, tetrahydrothienyl groups, and the like. Meanwhile, examples of the aromatic heterocyclic groups include 5 to 8-membered, preferably 5 or 6-membered monocyclic heteroaryl groups having 2 to 15 carbon atoms and containing at least one, preferably 1 to 3 hetero atoms such as nitrogen atoms, oxygen atoms, and sulfur atoms; and polycyclic or condensed-cyclic heteroaryl groups constituted of any of these monocyclic heteroaryl groups. Specifically, the aromatic heterocyclic groups include furyl groups, thienyl groups, pyridyl groups, pyrimidinyl groups, pyrazinyl groups, pyridazinyl groups, pyrazolyl groups, imidazolyl groups, oxazolyl groups, thiazolyl groups, benzofuryl groups, benzothienyl groups, quinolyl groups, isoquinolyl groups, quinoxalyl groups, phthalazinyl groups, quinazolinyl groups, naphthyridinyl groups, cinnolinyl groups, benzoimidazolyl groups, benzoxazolyl groups, benzothiazolyl groups, and the like.

Meanwhile, the optionally substituted cycloalkyl group represented by $R^{P1}$, $R^{P2}$, $R^{P3}$, or $R^{P4}$ includes 5-membered or 6-membered cycloalkyl groups, and preferred cycloalkyl groups include a cyclopentyl group, a cyclohexyl group, and the like. One or two or more substituents such as alkyl groups or alkoxy groups as listed as the substituents of the aryl group may be introduced onto the ring of the cycloalkyl group.

Moreover, the optionally substituted alkyl group represented by $R^{P1}$, $R^{P2}$, $R^{P3}$, or $R^{P4}$ include linear or branched alkyl groups having, for example, 1 to 15 carbon atoms, preferably 1 to 10 carbon atoms, and more preferably 1 to 6 carbon atoms. Specific examples thereof include a methyl group, an ethyl group, a n-propyl group, an isopropyl group, a n-butyl group, a s-butyl group, an isobutyl group, a t-butyl group, a pentyl group, a hexyl group, and the like. These alkyl groups may have one or two or more substituents, and examples of the substituents include alkoxy groups, halogen atoms, and the like. The alkoxy groups include the alkoxy groups listed as the substituents of the aryl group.

In addition, the ring which may be formed by $R^{P1}$ and $R^{P2}$ and/or $R^{P3}$ and $R^{N}$ includes four-membered rings, five-membered rings, and six-membered rings including the phosphorus atom to which $R^{P1}$ and $R^{P2}$ or $R^{P3}$ and $R^{N}$ are bound. Specifically, the rings include phosphetane rings, phospholane rings, phosphinane rings, 2,4-dimethylphosphetane rings, 2,4-diethylphosphetane rings, 2,5-dimethylphospholane rings, 2,5-diethylphospholane rings, 2,6-dimethyl phosphinane rings, 2,6-diethyl phosphinane rings, and the like. These rings may be optically active.

In addition, the optionally substituted divalent arylene group represented by Q includes arylene groups having 6 to 20 carbon atoms such as phenylene groups, biphenyldiyl groups, and binaphthalenediyl groups. The phenylene groups include o- and m-phenylene groups, and the phenylene groups may be substituted with any ones of alkyl groups having 1 to 4 carbon atoms such as methyl groups, ethyl groups, n-propyl groups, isopropyl groups, n-butyl groups, s-butyl groups, isobutyl groups, and t-butyl groups; alkoxy groups having 1 to 4 carbon atoms such as methoxy groups, ethoxy groups, n-propoxy groups, isopropoxy groups, n-butoxy groups, s-butoxy groups, isobutoxy groups, and t-butoxy groups; hydroxy groups; amino groups; substituted amino groups (substituents of the substituted amino groups include alkyl groups having 1 to 4 carbon atoms); and the like. The biphenyldiyl groups and the binaphthalenediyl groups preferably have a structure of the 1,1'-biaryl-2,2'-diyl type, and the biphenyldiyl groups and the binaphthalenediyl groups may be substituted with any ones of the alkyl groups and the alkoxy group described above, alkylenedioxy groups such as methylenedioxy groups, ethylenedioxy groups, and trimethylenedioxy groups, hydroxy groups, amino groups, substituted amino groups, and the like. In addition, the ferrocenediyl group may also have substituents, and the substituents include the alkyl groups, alkoxy groups, alkylenedioxy groups, hydroxy groups, amino groups, substituted amino groups, which are described above, and the like.

Specific examples of the diphosphines represented by general formula (B) include known diphosphines, and one of the known diphosphines is a compound represented by the following general formula (C):

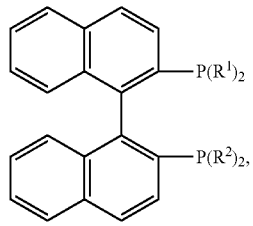

(C)

wherein $R^1$ and $R^2$ each independently represent a phenyl group which may be substituted with a substituent(s) selected from halogen atoms, alkyl groups, and alkoxy groups, a cyclopentyl group, or a cyclohexyl group.

Examples of the alkyl groups as the substituents in the phenyl group represented by the above-described $R^1$ or $R^2$ include linear or branched alkyl groups having 1 to 6 carbon atoms such as methyl groups and t-butyl groups. Examples of the alkoxy groups as the substituents in the phenyl group include linear or branched alkoxy groups having 1 to 6 carbon atoms such as methoxy groups and t-butoxy groups. Examples of the halogen atoms as the substituents in the phenyl group include chlorine atoms, bromine atoms, fluorine atoms, and the like. A plurality of these substituents may be introduced onto the phenyl group.

Specific examples of $R^1$ and $R^2$ include phenyl groups, p-tolyl groups, m-tolyl groups, o-tolyl groups, 3,5-xylyl groups, 3,5-di-t-butylphenyl groups, p-t-butylphenyl groups, p-methoxyphenyl groups, 3,5-di-t-butyl-4-methoxyphenyl groups, p-chlorophenyl groups, m-chlorophenyl groups, p-fluorophenyl groups, m-fluorophenyl groups, cyclobutane groups, cyclopentyl groups, cyclohexyl groups, isopropyl groups, and the like.

In addition, the binaphthyl ring, which is a basic skeleton of the compound represented by general formula (C), may be substituted with a substituent(s), and examples of the substituents include $C_1$ to $C_{20}$ alkyl groups such as methyl groups and t-butyl group; $C_1$ to $C_{20}$ alkoxy groups such as methoxy groups and t-butoxy groups; tri($C_1$ to $C_{20}$)alkylsilyl groups such as trimethylsilyl groups, triisopropylsilyl groups, and t-butyldimethylsilyl groups; and tri($C_1$ to $C_{20}$) arylsilyl groups such as triphenylsilyl groups.

In addition, another specific example of the diphosphines represented by general formula (B) is a compound represented by the following general formula (D):

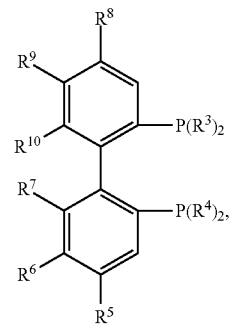

(D)

wherein $R^3$ and $R^4$ each independently represent a phenyl group which may be substituted with a substituent(s) selected from halogen atoms, alkyl groups, and alkoxy groups, a cyclopentyl group, or a cyclohexyl group; $R^5$, $R^6$, $R^7$, $R^8$, $R^9$, and $R^{10}$, which may be the same or different, each represent a hydrogen atom, an alkyl group, an alkoxy group, an acyloxy group, a halogen atom, a haloalkyl group, or a dialkylamino group; two of $R^5$, $R^6$, and $R^7$ may form an optionally substituted methylene chain or an optionally substituted (poly)methylenedioxy group; two of $R^8$, $R^9$, and $R^{10}$ may form an optionally substituted methylene chain or an optionally substituted (poly)methylenedioxy group; and $R^7$ and $R^{10}$ may form an optionally substituted methylene chain or an optionally substituted (poly)methylenedioxy group, provided that neither $R^7$ nor $R^{10}$ is a hydrogen atom.

Examples of the alkyl groups as the substituents in the phenyl group represented by the above-described $R^3$ or $R^4$ include linear or branched alkyl groups having 1 to 6 carbon atoms such as methyl groups and t-butyl groups. Examples of the alkoxy groups as the substituents in the phenyl group include linear or branched alkoxy groups having 1 to 6 carbon atoms such as methoxy groups and t-butoxy group. Examples of the halogen atoms as the substituents in the phenyl group include chlorine atoms, bromine atoms, fluorine atoms, and the like. A plurality of these substituents may be introduced onto the phenyl group. Specific examples of $R^3$ and $R^4$ include phenyl groups, p-tolyl groups, m-tolyl groups, o-tolyl groups, 3,5-xylyl groups, 3,5-di-t-butylphenyl groups, p-t-butylphenyl groups, p-methoxyphenyl groups, 3,5-di-t-butyl-4-methoxyphenyl groups, p-chlorophenyl groups, m-chlorophenyl groups, p-fluorophenyl groups, m-fluorophenyl groups, cyclobutane groups, cyclopentyl groups, cyclohexyl groups, isopropyl groups, and the like.

In addition, examples of the alkyl group represented by $R^5$ to $R^{10}$ include linear or branched alkyl groups having 1 to 6 carbon atoms such as a methyl group or a t-butyl group; examples of the alkoxy group represented by $R^5$ to $R^{10}$ include linear or branched alkoxy groups having 1 to 6 carbon atoms such as a methoxy group or a t-butoxy group; and examples of the acyloxy group represented by $R^5$ to $R^{10}$ include acyloxy groups having 2 to 10 carbon atoms such as an acetoxy group, a propanoyloxy group, a trifluoroacetoxy group, or a benzoyloxy group; examples of the halogen atom represented by $R^5$ to $R^{10}$ include a chlorine atom, a bromine atom, a fluorine atom, and the like; examples of the haloalkyl group represented by $R^5$ to $R^{10}$ include haloalkyl groups having 1 to 4 carbon atoms such as a trifluoromethyl group; and examples of the dialkylamino group represented by $R^5$ to $R^{10}$ include di($C_1$ to $C_{20}$)alkylamino groups such as a dimethylamino group and a diethylamino group.

When an optionally substituted methylene chain is formed by two of $R^5$, $R^6$, and $R^7$, or an optionally substituted methylene chain is formed by two of $R^8$, $R^9$, and $R^{10}$, the methylene chain is preferably, for example, a methylene chain having 3 to 5 carbon atoms, and specifically includes a trimethylene group, a tetramethylene group, a pentamethylene group, and the like. In addition, the substituent (s) in the optionally substituted methylene chain include alkyl groups, halogen atoms, and the like, and specific examples thereof include the above-described alkyl groups having 1 to 6 carbon atoms, fluorine atoms, and the like.

In addition, when an optionally substituted methylene chain is formed by two of $R^5$, $R^6$, and $R^7$, when an optionally substituted methylene chain is formed by two of $R^8$, $R^9$, and $R^{10}$, or when an optionally substituted methylene chain is formed by $R^7$ and $R^{10}$, specific examples of the methylene chain include methylene chains having 1 to 4 carbon atoms such as a methylene group, an ethylene group, a trimethylene group, and a propylene group. In addition, the substituent (s) introduced onto the methylene chain include alkyl groups, halogen atoms, and the like, and specific examples thereof include the above-described alkyl groups having 1 to 6 carbon atoms, fluorine atoms, and the like.

Meanwhile, when an optionally substituted (poly)methylenedioxy group is formed by two of $R^5$, $R^6$, and $R^7$, when an optionally substituted (poly)methylenedioxy group is formed by two of $R^8$, $R^9$, and $R^{10}$, or when an optionally substituted (poly)methylenedioxy group is formed by $R^7$ and $R^{10}$, specific examples of the (poly)methylenedioxy group include (poly)methylenedioxy groups having 1 to 4 carbon atoms such as a methylenedioxy group, an ethylenedioxy group, and a trimethylenedioxy group. In addition, the substituent(s) introduced onto the (poly)methylenedioxy group include alkyl groups, halogen atoms, and the like, and specific examples thereof include the above-described alkyl groups having 1 to 6 carbon atoms, fluorine atoms, and the like.

Specific examples of the optically active diphosphine include 2,2'-bis(diphenylphosphino)-1,1'-binaphthyl, 2,2'-bis[di(p-tolyl)phosphino]-1,1'-binaphthyl(tolbinap), 2,2'-bis[di(m-tolyl)phosphino]-1,1'-binaphthyl, 2,2'-bis[di(3,5-xylyl)phosphino]-1,1'-binaphthyl(xylbinap), 2,2'-bis[di(p-t-butylphenyl)phosphino]-1,1'-binaphthyl, 2,2'-bis[di(p-methoxyphenyl)phosphino]-1,1'-binaphthyl, 2,2'-bis[di(3,5-di-t-butyl-4-methoxyphenyl)phosphino]-1,1'-binaphthyl, 2,2'-bis[di(cyclopentyl)phosphino]-1,1'-binaphthyl, 2,2'-bis[di(cyclohexyl)phosphino]-1,1'-binaphthyl, 2,2'-bis(diphenylphosphino)-5,5',6,6',7,7',8,8'-octahydro-1,1'-binaphthyl, 2,2'-bis(di-p-tolylphosphino)-5,5',6,6',7,7',8,8'-octahydro-1,1'-binaphthyl, 2,2'-bis(di-m-tolylphosphino)-5,5',6,6',7,7',8,8'-octahydro-1,1'-binaphthyl(xylyl-H8-binap), 2,2'-bis(di-3,5-xylylphosphino)-5,5',6,6',7,7',8,8'-octahydro-1,1'-binaphthyl, 2,2'-bis(di-p-t-butylphenylphosphino)-5,5',6,6',7,7',8,8'-octahydro-1,1'-binaphthyl, 2,2'-bis(di-p-methoxyphenylphosphino)-5,5',6,6',7,7',8,8'-octahydro-1,1'-binaphthyl, 2,2'-bis(di-p-chlorophenylphosphino)-5,5',6,6',7,7',8,8'-octahydro-1,1'-binaphthyl, 2,2'-bis(dicyclopentylphosphino)-5,5',6,6',7,7',8,8'-octahydro-1,1'-binaphthyl, 2,2'-bis(dicyclohexylphosphino)-5,5',6,6',7,7',8,8'-octahydro-1,1'-binaphthyl, ((4,4'-bi-1,3-benzodioxole)-5,5'-diyl)bis(diphenylphosphine) (segphos), (4,4'-bi-1,3-benzodioxole)-5,5'-diyl)bis(di(3,5-xylyl)phosphine) (dm-segphos), ((4,4'-bi-1,3-benzodioxole)-5,5'-diyl)bis(di(3,5-di-t-butyl-4-methoxyphenyl)phosphine), ((4,4'-bi-1,3-benzodioxole)-5,5'-diyl)bis(di(4-methoxyphenyl)1)phosphine), ((4,4'-bi-1,3-benzodioxole)-5,5'-diyl)bis(dicyclohexylphosphine), ((4,4'-bi-1,3-benzodioxole)-5,5'-diyl)bis(bis(3,5-di-t-buty 1-phenyl)phosphine), 2,2'-bis(di-3,5-xylylphosphino)-6,6'-dimethoxy-1,1'-biphenyl (xylyl-MeO-biphep), 2,2'-bis(diphenylphosphino)-6,6'-dimethyl-1,1-biphenyl, 2,2'-bis(di-p-tolylphosphino)-6,6'-dimethyl-1,1'-biphenyl, 2,2'-bis(di-o-tolylphosphino)-6,6'-dimethyl-1,1'-biphenyl, 2,2'-bis(di-m-fluorophenylphosphino)-6,6'-dimethyl-1,1'-biphenyl, 2,2'-bis(diphenylphosphino)-6,6'-dimethoxy-1,1'-biphenyl, 2,2'-bis(di-p-tolylphosphino)-6,6'-dimethoxy-1,1'-biphenyl, 2,2',6,6'-tetramethoxy-4,4'-bis(di-3,5-xylylphosphino)-3,3'-bipyridine (xylyl-p-phos), 2,2',6,6'-tetramethoxy-4,4'-bis(diphenylphosphino)-3,3'-bipyridine, 2,2',6,6'-tetramethoxy-4,4'-bis(di-p-tolylphosphino)-3,3'-bipyridine, 2,2',6,6'-tetramethoxy-4,4'-bis(di-o-tolylphosphino)-3,3'-bipyridine, 4,12-bis(di-3,5-xylylphosphino)-[2.2]-paracyclophane, 4,12-bis(diphenylphosphino)-[2.2]-paracyclophane, 4,12-bis(di-p-tolylphosphino)-[2.2]-paracyclophane, 4,12-bis(di-o-tolylphosphino)-[2.2]-paracyclophane, 1,1'-bis(2,4-diethylphosphotano)ferrocene, 1,13-bis(diphenylphosphino)-7,8-dihydro-6H-dibenzo[f,h][1,5]dioxonin, 1,13-bis(bis(3,5-dimethylphenyl)phosphino)-7,8-dihydro-6H-dibenzo[f,h][1,5]dioxonin (xylyl-C3-tunephos), 6,6'-bis(bis(3,5-dimethylphenyl)phosphino)-2,2',3,3'-tetrahydro-5,5'-bi-1,4-benzodioxin (xylyl-synphos), and the like.

Besides the above-described diphosphines, specific examples of the diphosphines usable in the present invention include N,N-dimethyl-1-[1',2-bis(diphenylphosphino)ferrocenyl]ethyl amine, 2,3-bis(diphenylphosphino)butane, 1-cyclohexyl-1,2-bis(diphenylphosphino)ethane, 2,3-O-isopropylidene-2,3-dihydroxy-1,4-bis(diphenylphosphino) butane, 1,2-bis[(o-methoxyphenyl)phenylphosphino]ethane, 1,2-bis(2,5-dimethylphospholano)ethane, N,N'-bis(diphenylphosphino)-N,N'-bis(1-phenylethyl)ethylene diamine, 1,2-bis(diphenylphosphino)propane, 2,4-bis(diphenylphosphino)pentane, cyclohexylanisylmethylphosphine, 2,3-bis(diphenylphosphino)-5-norbornene, 3,4-bis(diphenylphosphino)-1-benzylpyrrolidine, 1-[1',2-bis(diphenylphosphino)ferrocenyl]ethyl alcohol, 2,2'-bis(diphenylphosphino)-1,1'-dicyclopentane, 2,2'-bis(diphenylphosphino)-1,1-binaphthyl-5,5'-disulfonic acid sodium salt, 2,2'-bis(di(3,5-xylyl)phosphino)-1,1-binaphthyl-5,5'-disulfonic acid sodium salt, 1,1-(2,2'-bis(diphenylphosphino)-1,1'-binaphthyl-6,6'-diyl)bis(methylene)guanidine, 1,1-(2,2'-bis(di(3,5-xylyl)phosphino)-1,1'-binaphthyl-6,6'-diyl)bis(methylene)guanidine, (6,6'-bis(tris(3,3,4,4,5,5,6,6,7,7,8,8,8-tridecafluorooctyl)silyl)-1,1'-binaphthyl-2,2'-diyl)bis(diphenylphosphine), (6,6'-bis(tris(3,3,4,4,5,5,6,6,7,7,8,8,8-tridecafluorooctyl)silyl)-1,1'-binaphthyl-2,2'-diyl)bis(di(3,5-xylyl)phosphine), (2,2'-bis(diphenylphosphino)-1,1'-binaphthyl-4,4'-diyl)dimethanamine•hydrobromide, (2,2'-bis(di(3,5-xylyl)phosphino)-1,1'-binaphthyl-4,4'-diyl)dimethanamine•hydrobromide, (4,4'-bis(trimethylsilyl)-1,1'-binaphthyl-2,2'-diyl)bis(diphenylphosphine), (4,4'-bis(trimethylsilyl)-1,1'-binaphthyl-2,2'-diyl)bis(di(3,5-xylyl)phosphine), (4,4'-bis(triisopropylsilyl)-1,1'-binaphthyl-2,2'-diyl)bis(diphenylphosphine), (4,4'-bis(triisopropylsilyl)-1,1'-binaphthyl-2,2'-diyl)bis(di(3,5-xylyl)phosphine), 2,2'-bis(diphenylphosphino)-1,1'-binaphthyl-4,4'-diyldiphosphonic acid, 2,2'-bis(di(3,5-xylyl)phosphino)-1,1'-binaphthyl-4,4'-diyldiphosphonic acid, tetraethyl 2,2'-bis(diphenylphosphino)-1,1'-binaphthyl-4,4'-diyldiphosphonate, tetraethyl 2,2'-bis(di(3,5-xylyl)phosphino)-1,1'-binaphthyl-4,4'-diyldiphosphonate, (4,4'-diphenyl-1,1'-binaphthyl-2,2'-diyl)bis(diphenylphosphine), (4,4'-diphenyl-1,1'-binaphthyl-2,2'-diyl)bis(di(3,5-xylyl)phosphine), (4,4'-dichloro-1,1'-binaphthyl-2,2'-diyl)bis(diphenylphosphine), (4,4'-dichloro-1,1'-binaphthyl-2,2'-diyl)bis(di(3,5-xylyl)phosphine), (4,4'-dibromo-1,1'-binaphthyl-2,2'-diyl)bis(diphenylphosphine), (4,4'-dibromo-1,1'-binaphthyl-2,2'-diyl)bis(di(3,5-xylyl)phosphine), (4,4'-dimethyl-1,1'-binaphthyl-2,2'-diyl)bis(diphenylphosphine), (4,4'-dimethyl-1,1'-binaphthyl-2,2'-diyl)bis(di(3,5-xylyl)phosphine), (2,2'-bis(diphenylphosphino)-1,1'-binaphthyl-4,4'-diyl)bis(diphenylmethanol), (2,2'-bis(di(3,5-xylyl)phosphino)-1,1'-binaphthyl-4,4'-diyl) bis(diphenylmethanol), (4,4'-bis(1,1,1,2,2,3,3,4,4,5,5,6,6,8,8,9,9,10,10,11,11,12,12,13,13,13-hexacosafluoro-7-(perfluorohexyl)tridecan-7-yl)-1,1'-binaphthyl-2,2'-diyl)bis(diphenylphosphine), (4,4'-bis(1,1,1,2,2,3,3,4,4,5,5,6,6,8,8,9,9,10,10,11,11,12,12,13,13,13-hexacosafluoro-7-(perfluorohexyl)tridecan-7-yl)-1,1'-binaphthyl-2,2'-diyl)bis(di(3,5-xylyl)phosphine), (7,7'-dimethoxy-1,1'-binaphthyl-2,2'-diyl)bis(diphenylphosphine), (7,7'-dimethoxy-1,1'-binaphthyl-2,2'-diyl)bis(di(3,5-xylyl) phosphine), 4,4'-di-tert-butyl-4,4',5,5'-tetrahydro-3H,3'H-3,3'-bidinaphtho[2,1-c:1',2'-e]phosphapine, 1,2-bis(3H-dinaphtho[2,1-c:1',2'-e]phosphapin-4(5H)-yl)benzene, 3,3'-bis(diphenylphosphino)-4,4'-biphenanthrene, 3,3'-bis(di(3,5-xylyl)phosphino)-4,4'-biphenanthrene, (3,3'-diphenyl-1,1'-binaphthyl-2,2'-diyl)bis(methylene)bis(diphenylphosphine), (3,3'-diphenyl-1,1'-binaphthyl-2,2'-diyl)bis(methylene)bis(di(3,5-xylyl)phosphine), 2,2'-bis(diphenylphosphinoxy)-1,1'-binaphthyl, 2,2'-bis(di(3,5-xylyl)phosphinoxy)-1,1'-binaphthyl, (3,3'-dimethyl-1,1'-binaphthyl-2,2'-diyl)bis(oxy)bis(diphenylphosphine), (3,3'-dimethyl-1,1'-binaphthyl-2,2'-diyl)bis(oxy)bis(di(3,5-xylyl)phosphine), (3,3'-diphenyl-1,1'-binaphthyl-2,2'-diyl)bis(oxy)bis(diphenylphosphine), (3,3'-diphenyl-1,1'-binaphthyl-2,2'-diyl)bis(oxy)bis(di(3,5-xylyl)phosphine), (3,3'-bis(3,5-dimethylphenyl)-1,1'-binaphthyl-2,2'-diyl)bis(oxy)bis(diphenylphosphine), (3,3'-bis(3,5-dimethylphenyl)-1,1'-binaphthyl-2,2'-diyl)bis(oxy)bis(di(3,5-xylyl)phosphine), (3,3'-diphenyl-1,1'-binaphthyl-2,2'-diyl)bis(oxy)bis(bis(3,5-dimethylphenyl)phosphine), N2,N2'-bis(diphenylphosphino)-1,1'-binaphthyl-2,2'-diamine, N2,N2'-bis(di(3,5-xylyl)phosphino)-1,1'-binaphthyl-2,2'-diamine, (SP)-1-[(S)-α-(dimethylamino)-2-(diphenylphosphino)benzyl]-2-diphenylphosphinoferrocene, (RP)-1-[(R)-α-(dimethylamino)-2-(diphenylphosphino)benzyl]-2-diphenylphosphinoferrocene, (R)-1-{(RP)-2-[2-(diphenylphosphino)phenyl]ferrocenyl}ethyl diphenylphosphine, (S)-1-{(SP)-2-[2-(diphenylphosphino)phenyl]ferrocenyl}ethyl diphenylphosphine, (R)-1-{(RP)-2-[2-(diphenylphosphino)phenyl]ferrocenyl}ethyl dicyclophosphine, (S)-1-{(SP)-2-[2-(diphenylphosphino)phenyl]ferrocenyl}ethyl dicyclophosphine, (R)-1-{(RP)-2-[2-(diphenylphosphino)phenyl]ferrocenyl}ethyl di(2-norbonyl)phosphine, (S)-1-{SP)-2-[2-(diphenylphosphino)phenyl]ferrocenyl}ethyl di(2-norbonyl)phosphine, (R)-1-{(RP)-2-[2-(diphenylphosphino)phenyl]ferrocenyl}ethyl di(3,5-xylyl)phosphine, (S)-1-{(SP)-2-[2-(diphenylphosphino)phenyl]ferrocenyl}ethyl di(3,5-xylyl)phosphine, (R)-1-{(RP)-2-[2-[di(3,5-xylyl)phosphino]phenyl]ferrocenyl}ethyldi(3,5-xylyl)phosphine, (S)-1-{(SP)-2-[2-[di(3,5-xylyl)phosphino]phenyl]ferrocenyl}ethyldi(3,5-xylyl)phosphine, (R)-1-{(RP)-2-[2-(diphenylphosphino)phenyl]ferrocenyl}ethyl bis[3,5-bis-(trifluoromethyl)phenyl]phosphine, (S)-1-{(SP)-2-[2-(diphenylphosphino)phenyl]ferrocenyl}ethyl bis[3,5-bis-(trifluoromethyl)phenyl]phosphine, (R)-1-{(RP)-2-[2-[bis(4-methoxy-3,5-dimethylphenyl)phosphino]phenyl]ferrocenyl}ethylbis[3,5-bis(trifluoromethyl)phenyl]phosphine, (S)-1-{(SP)-2-[2-[bis(4-methoxy-3,5-dimethylphenyl)phosphino]phenyl]ferrocenyl}ethylbis[3,5-bis(trifluoromethyl)phenyl]phosphine, 3,3',4,4'-tetramethyl-1,1'-diphenyl-2,2',5,5'-tetrahydro-1H,1'H-2,2'-biphosphole, 1,1'-di-tert-butyl-2,2'-biphospholane, 2,2'-di-tert-butyl-2,2',3,3'-tetrahydro-1H,1'H-1,1'-bisisophosphindole, 1,2-bis(2,4-dimethylphosphetan-1-yl)ethane, 1,2-bis(2,5-dimethylphospholan-1-yl)ethane, 1,2-bis(2,4-dimethylphosphetan-1-yl)benzene, 1,2-bis(2,5-dimethylphospholan-1-yl)benzene, 3,4-bis(2,5-dimethylphospholan-1-yl)furan-2,5-dione, 3,4-bis(2,5-diethylphospholan-1-yl)furan-2,5-dione, 3,4-bis(2,5-dimethylphospholan-1-yl)-1-phenyl-1H-pyrrole-2,5-dione, 1-(3,5-bis(trifluoromethyl)phenyl)-3,4-bis(2,5-dimethylphospholan-1-yl)-1H-pyrrole-2,5-dione, 1-((1R,2S,4R,5S)-2,5-dimethyl-7-phosphabicyclo[2.2.1]heptan-7-yl)-2-H2R,5S)-2,5-dimethyl-7-phosphabicyclo[2.2.1]hepta ne-7-yl)benzene, 1,1'-(benzo[b]thiophene-2,3-diyl)bis(2,5-dimethylphospholane), (2,2',4,4'-tetramethyl-3,3',4,4'-tetrahydro-2H,2'H-6,6'-bibenzo[b][1,4]dioxepin-7,7'-diyl)bis(diphenylphosphine), (2,2',4,4'-tetramethyl-3,3',4,4'-tetrahydro-2H,2'H-6,6'-bibenzo[b][1,4]dioxepin-7,7'-diyl)bis(di(3,5-xylyl)phosphine), ((6R)-6,7-dimethyl-6,7-dihydrodibenzo[e,g][1,4]dioxocin-1,12-diyl)bis(diphenylphosphine), ((6R)-6,7-dimethyl-6,7-dihydrodibenzo[e,g][1,4]dioxocin-1,12-diyl)bis(di(3,5-xylyl)phosphine), (4,4',5,5',6,6'-hexamethylbiphenyl-2,2'-diyl)bis(diphenylphosphine), (4,4',5,5',6,6'-hexamethylbiphenyl-2,2'-diyl)bis(di(3,5-xylyl)phosphine), (4,4',5,5',6,6'-hexamethoxybiphenyl-2,2'-diyl)bis(diphenylphosphine), (4,4',5,5',6,6'-hexamethoxybiphenyl-2,2'-diyl)bis(di(3,5-xylyl)phosphine), (5,5'-dichloro-4,4',6,6'-tetramethylbiphenyl-2,2'-diyl)bis(diphenylphosphine), (5,5'-dichloro-4,4',6,6'-tetramethylbiphenyl-2,2'-diyl)bis(di(3,5-xylyl)phosphine), (5,5'-dimethoxy-4,4',6,6'-tetramethylbiphenyl-2,2'-diyl)bis(diphenylphosphine), (5,5'-dimethoxy-4,4',6,6'-tetramethylbiphenyl-2,2'-diyl)bis (di(3,5-xylyl)phosphine), 2,2'-bis(diphenylphosphino)-6,6'-dimethoxybiphenyl-3,3'-diol, 2,2'-bis(di(3,5-xylyl)phosphino)-6,6'-dimethoxybiphenyl-3,3'-diol, (3,3',6,6'-tetramethoxybiphenyl-2,2'-diyl)bis(diphenylphosphine), (3,3',6,6'-tetramethoxybiphenyl-2,2'-diyl)bis(di(3,5-xylyl)phosphine), (3,3'-diisopropyl-6,6'-dimethoxybiphenyl-2,2'-diyl)bis(diphenylphosphine), (3,3'-diisopropyl-6,6'-dimethoxybiphenyl-2,2'-diyl)bis(di(3,5-xylyl)phosphine), (6,6'-dimethoxy-3,3'-bis(p-tolyloxy)biphenyl-2,2'-diyl)bis(diphenylphosphine), (6,6'-dimethoxy-3,3'-bis(p-tolyloxy)biphenyl-2,2'-diyl)bis(di(3,5-xylyl)phosphine), 2,2'-bis(diphenylphosphino)-6,6'-dimethoxybiphenyl-3,3'-diylbis(2,2-dimethylpropanoate), 2,2'-bis(di(3,5-xylyl)phosphino)-6,6'-dimethoxybiphenyl-3,3'-diylbis(2,2-dimethylpropanoate), (5,5'-dichloro-6,6'-dimethoxybiphenyl-2,2'-diyl)bis(diphenylphosphine), (5,5'-dichloro-6,6'-dimethoxybiphenyl-2,2'-diyl)bis(di(3,5-xylyl)phosphine), 6,6'-bis(diphenylphosphino)biphenyl-2,2'-diyl diacetate, 6,6'-bis(di(3,5-xylyl)phosphino)biphenyl-2,2'-diyl diacetate, 6,6'-bis(diphenylphosphino)biphenyl-2,2'-diylbis(2,2-dimethylpropanoate), 6,6'-bis(di(3,5-xylyl)phosphino)biphenyl-2,2'-diylbis(2,2-dimethylpropanoate), 6,6'-bis(diphenylphosphino)biphenyl-2,2'-diylbis(2-methylpropanoate), 6,6'-bis(di(3,5-xylyl)phosphino)biphenyl-2,2'-diylbis(2-methylpropanoate), 6,6'-bis(diphenylphosphino)biphenyl-2,2'-diyldicyclohexanecarboxylate, 6,6'-bis(di(3,5-xylyl)phosphino)biphenyl-2,2'-diyldicyclohexanecarboxylate, (4,4',6,6'-tetrakis(trifluoromethyl)biphenyl-2,2'-diyl)bis(diphenylphosphine), (4,4',6,6'-tetrakis(trifluoromethyl)biphenyl-2,2'-diyl)bis(di(3,5-xylyl)phosphine), (5-methoxy-4,6-dimethyl-4',6'-bis(trifluoromethyl)biphenyl-2,2'-diyl)bis(diphenylphosphine), (5-methoxy-4,6-dimethyl-4',6'-bis(trifluoromethyl)biphenyl-2,2'-diyl)bis(di(3,5-xylyl)phosphine), (2,2,2',2'-tetramethyl-4,4'-bibenzo[d][1,3]dioxole-5,5'-diyl)bis(diphenylphosphine), (2,2,2',2'-tetramethyl-4,4'-bibenzo[d][1,3]dioxole-5,5'-diyl)bis(di(3,5-xylyl)phosphine), 6,6'-bis(diphenylphosphino)-2,2',3,3'-tetrahydro-7,7'-bibenzofuran, 6,6'-bis(di(3,5-xylyl)phosphino)-2,2',3,3'-tetrahydro-7,7'-bibenzofuran, (2,2,2',2'-tetrafluoro-4,4'-bibenzo[d][1,3]dioxole-5,5'-diyl)bis(diphenylphosphine), (2,2,2',2'-tetrafluoro-4,4'-bibenzo[d][1,3]dioxole-5,5'-diyl)bis(di(3,5-xylyl)phosphine), 2-(naphthyl)-8-diphenylphosphino-1-[3,5-dioxa-4-phosphacyclohepta[2,1-a; 3,4-a']dinaphthalene-4-yl]-1,2-dihydroquinoline, 4,12-bis(di(3,5-xylyl)phosphino)-[2.2]-paracyclophane, 7,7'-bis(di(3,5-xylyl)phosphino)-2,2',3,3'-tetrahydro-1,1'-spirobiindane (Xyl-SDP), 7,7'-bis(diphenylphosphino)-2,2',3,3'-tetrahydro-1,1'-spirobiindane (SDP), bis(2-diphenylphosphinophenyl)ether (DPEphos), 4,5-bis(diphenylphosphinomethyl)-2,2-dimethyl-1,3-dioxolane (DIOP), 1,2-bis(diphenylphosphino)propane (PROPHOS), 2,3-bis(diphenylphosphino)butane (CHIRAPHOS), 1,2-bis[(2-methoxyphenyl)(phenyl)phosphinolethane (DIPAMP), 3,4-bis(diphenylphosphino)-1-benzylpyrrolidine (DEGUPHOS), 2,3-bis(diphenylphosphino)-bicyclo[2.2.1]hept-5-ene (NORPHOS), 1-tertiary-butoxycarbonyl-4-diphenylphosphino-2-(diphenylphosphinomethyl)pyrrolidine (BPPM), (2,2'-bis-(dibenzofuran-3,3-diyl)-bis-diphenylphosphine (BIBFUP), 2,2'-bis(diphenylphosphino)-3,3-binaphtho[b]furan (BINAPFu), 2,2'-bis(diphenylphosphino)-3,3'-bi[benzo[b]thiophene] (BITIANP), N,N'-dimethyl-7,7'-bis(di(3,5-xylyl)phosphino)-3,3',4,4'-tetrahydro-8,8'-bi-2H-1,4-benzoxazine (Xyl-Solphos), 2,3-bis(tertiary-butylmethylphosphino)quinoxaline (QuinoxP*), 2,4-bis(diphenylphosphino)pentane (SKEWPHOS), 2,4-bis(di(3,5-xylyl)phosphino)pentane (XylSKEWPHOS), 4,4'-bis(diphenylphosphino)-2,2',5,5'-tetramethyl-3,3'-bithiophene (TMBTP), 3,3'-bis(diphenylphosphonyl)-1,1'-2,2'-biindole (N-Me-2-BINPO), (2,2',5,5'-tetramethyl-3,3'-bithiophene-4,4'-diyl)bis(diphenylphosphine) (BITIANP), (4,4',6,6'-tetramethyl-3,3'-bibenzo[b]thiophene-2,2'-diyl)bis(diphenylphosphine) (tetraMe-BITIANP), 1,1'-bis(diphenylphosphino)-3,3'-dimethyl-1H,1'H-2,2'-biindole (BISCAP), 2,2'-bis(diphenylphosphino)-3,3'-bibenzofuran (BICUMP), 2,2'-bis(diphenylphosphino)-1,1'-benzo[d]imidazole (BIMIP), 1,3-bis(diphenylphosphino)propane, 1,4-bis(diphenylphosphino)butane, bis(2-(diphenylphosphino)ethyl)amine, 2-(diphenylphosphino)ethaneamine, and the like.

The following are specific examples of the transition metal complex:

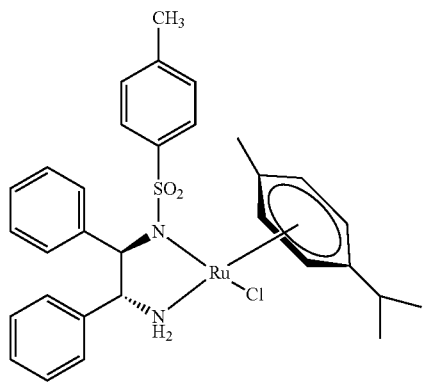

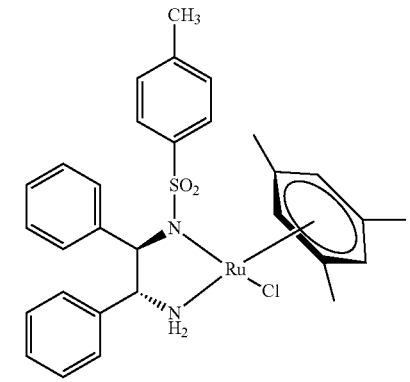

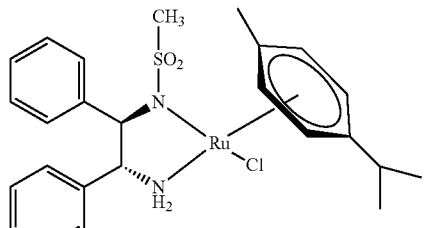

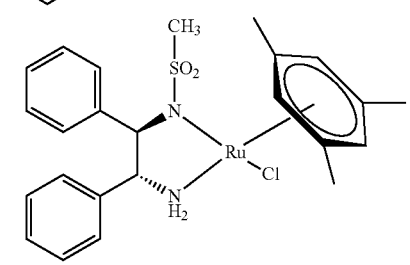

-continued
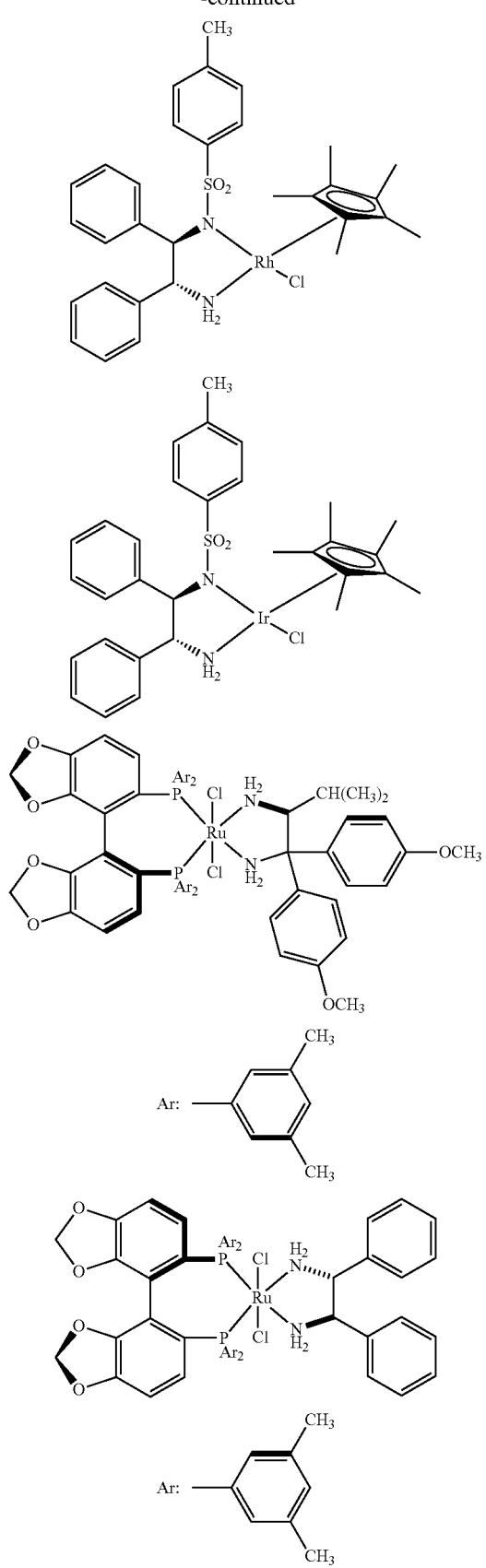
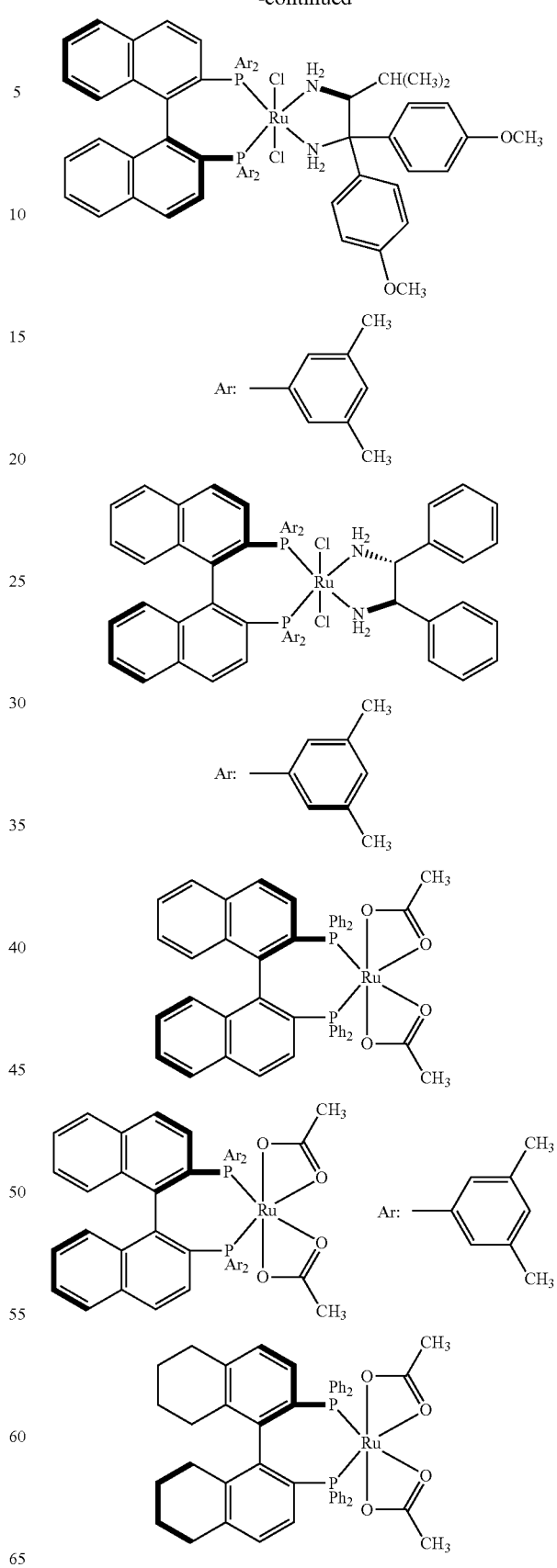

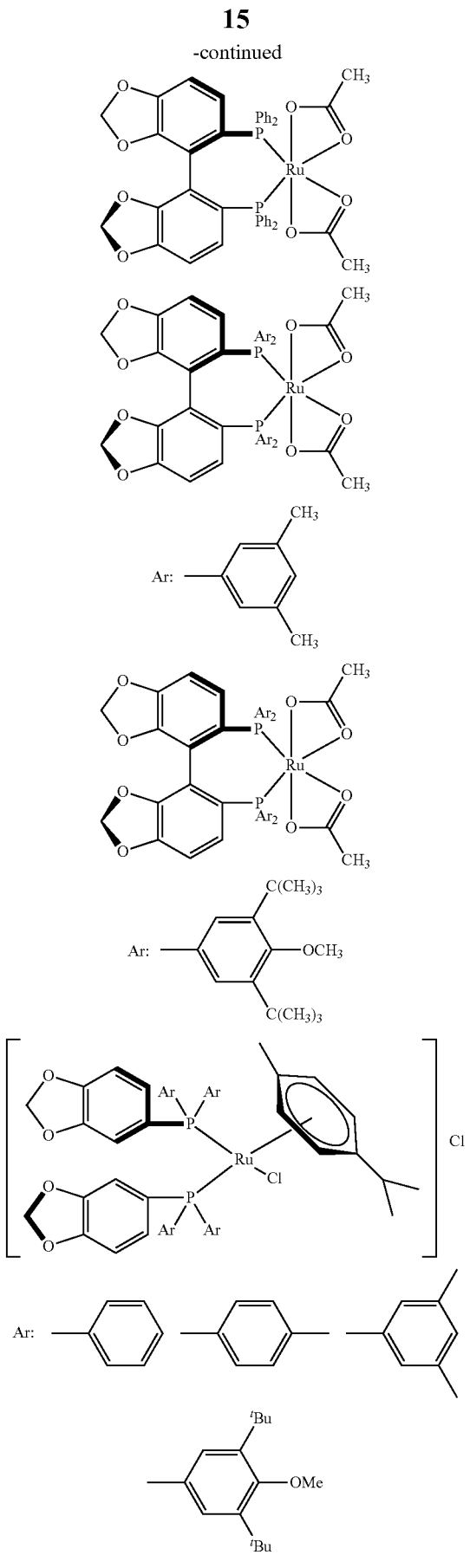

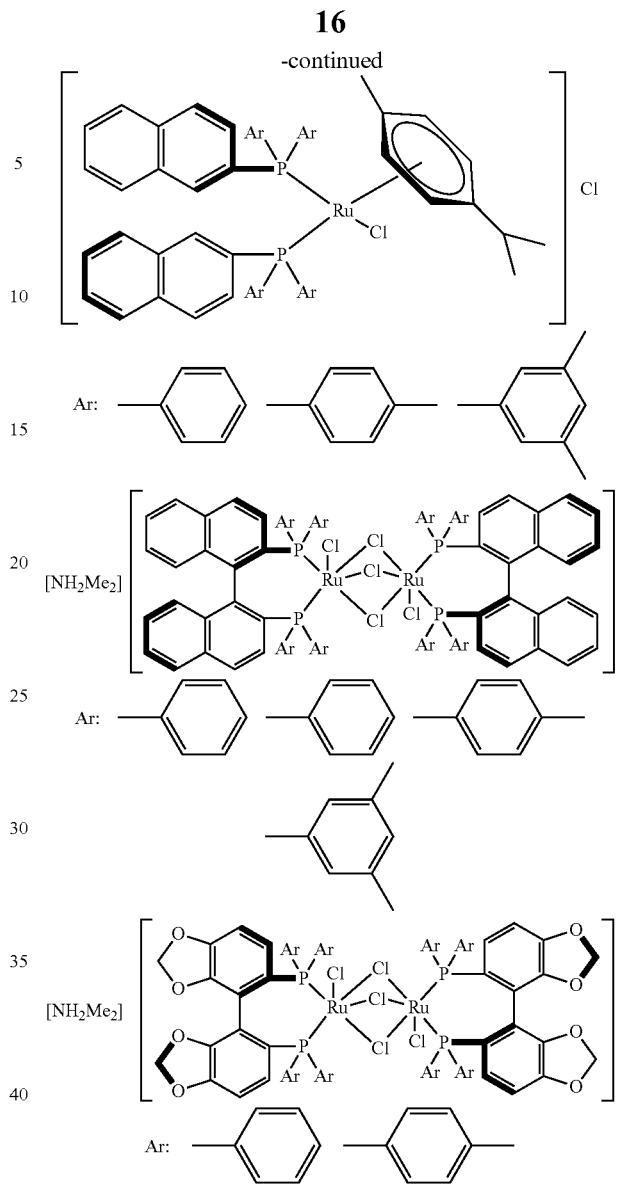

The nitrogen-containing compound added in the present invention includes aliphatic amines, aromatic amines, and nitrogen-containing heterocyclic compounds. Of these, nitrogen-containing compounds having two or more nitrogen atoms are preferable.

An aliphatic amine means a compound in which a hydrogen atom(s) of ammonia ($NH_3$) is(are) replaced by an aliphatic group(s). The aliphatic groups include linear or branched alkyl groups having 1 to 10 carbon atoms and alicyclic groups. Linear or branched alkyl groups having 1 to 6 carbon atoms and alicyclic groups are preferable. Specifically, examples of the aliphatic amines include methylamine, ethylamine, propylamine, butylamine, isopropylamine, 2-ethylhexylamine, tert-butylamine, diethylamine, diisopropylamine, triethylamine, tributylamine, diethylenetriamine, triethylenetetramine, tris(2,2',2''-aminoethyl)amine, N,N'-bis(2-aminoethyl)-1,3-propanediamine, N,N'-bis(3-aminopropyl)ethylenediamine, bis(3-aminopropyl)amine, 1,2-bis(3-aminopropylamino)ethane, 1,4-bis(3-aminopropyl)piperidine, cyclopropylamine, cyclohexylamine, and the like. The aliphatic amine is preferably diethylenetriamine, triethylenetetramine, tris(2,2',2''-aminoethyl)amine, N,N'-bis(2-aminoethyl)-1,3-propanediamine, N,N'-bis(3-aminopropyl)ethylenediamine, bis(3-aminopropyl)amine, 1,2-bis(3-aminopropylamino)ethane, 1,4-bis(3-aminopropyl)piperidine, or the like, and more preferably diethylenetriamine or triethylenetetramine.

An aromatic amine means a compound in which a hydrogen atom(s) of ammonia is(are) replaced by an aromatic group(s). The aromatic groups include monocyclic or polycyclic (condensed cyclic) aromatic groups having aromaticity. Specific examples of the aromatic amines include aniline, toluidine, xylidine, anisidine, naphthylamine, diphenylamine, triphenylamine, benzidine, 1,2-phenylenediamine, 4-fluoro-1,2-phenylenediamine, 2,3-diaminopyridine, 3,4-diaminopyridine, 2,3-diaminotoluene, 3,4-diaminotoluene, 3,3'-diaminobenzene, 3,4-diaminobenzophenone, 2,5-diamino-5-bromopyridine, 6,6'-diamino-2,2'-dipyridyl, 4,5-dichloro-1,2-phenylenediamine, 3,4-diaminobenzoic acid, 2,2'-dipyridyl, 2,2'-bi-4-picoline, 6,6'-bi-3-picoline, phthalocyanine, 2,2'-bisquinoline, and the like. Preferred aromatic amines include 1,2-phenylenediamine, 4-fluoro-1,2-phenylenediamine, 2,3-diaminopyridine, 3,4-diaminopyridine, 2,3-diaminotoluene, 3,4-diaminotoluene, 3,3'-diaminobenzene, 3,4-diaminobenzophenone, 2,5-diamino-5-bromopyridine, 6,6'-diamino-2,2'-dipyridyl, 4,5-dichloro-1,2-phenylenediamine, 3,4-diaminobenzoic acid, 2,2'-dipyridyl, 2,2'-bi-4-picoline, 6,6'-bi-3-picoline, phthalocyanine, 2,2'-biquinoline, and the like. 1,2-Phenylenediamine and 3,4-diaminobenzoic acid are more preferable.

The nitrogen-containing heterocyclic compounds include aromatic compounds such as pyrrole, pyridine, imidazole, 2-methylimidazole, 1-methylimidazole, 1,3-thiazole, oxazole, pyrazole, 1,2,4-triazole, pyrazine, pyrimidine, pyridazine, indole, quinoline, and purine; and endocyclic aliphatic amines such as diazabicycloundecane (DBU), piperidine, diazabicyclooctane (DABCO), and sparteine. Preferred nitrogen-containing heterocyclic compounds include imidazole, 2-methylimidazole, 1-methylimidazole, 1,3-thiazole, 1,3-oxazole, pyrazole, 1,2,4-triazole, and the like. Imidazoles such as 2-methylimidazole, 1-methylimidazole, and imidazole are more preferable.

The amount of the nitrogen-containing compound added is not less than one, preferably two, and more preferably three times the number of moles of the transition metal complex, when the nitrogen-containing compound has one nitrogen atom, or is not less than 1 and preferably 1.5 times the number of moles of the transition metal complex, when the nitrogen-containing compound has two or more nitrogen atoms.

Especially after an asymmetric reduction reaction using an optically active transition metal complex as a catalyst, the present invention makes it possible to avoid the decrease in optical purity of the product without separating the catalyst.

Asymmetric reduction methods conducted in the production method of the present invention includes asymmetric hydrogenation reactions, asymmetric hydrogen transfer reactions, and the like.

The asymmetric hydrogenation reactions are not particularly limited, and include a method for producing an optically active alcohol by asymmetric hydrogenation of a carbonyl group (for example, Documents (5th ed., Jikken Kagaku Kouza 19, organic compound synthesis VII, Maruzen Company, Limited, p. 122) etc.), and a method for producing an optically active compound by asymmetric hydrogenation of a carbon-carbon double bond, an imino group, or the like (for example, Documents (Asymmetric Catalysis In Organic Synthesis, p. 16 to p. 94) etc.).

The asymmetric hydrogen transfer reactions are not particularly limited, and examples thereof include a method for producing an optically active alcohol by asymmetric reduction of a carbonyl group as described in Documents (J. Am. Chem. Soc., 1997, 119, 8738, J. Am. Chem. Soc. 1996, 118, 2521, etc.), and the like.

In the production method of the present invention, after the nitrogen-containing compound is added to a reaction solution in which the reduction reaction has been conducted by using the transition metal complex, reaction solvent recovery and/or distillation are/is performed.

EXAMPLES

Hereinafter, the present invention will be described in detail based on Examples. However, the present invention is not limited to these examples. Note that, in the following Examples and Comparative Examples, the MS spectrum was measured with an LCMS-IT-TOF apparatus manufactured by SHIMADZU. In addition, the GC analysis was conducted with GC: Chirasil Dex-CB (0.25 mm×25 m, DF=0.25).

Example 1

To a 200 ml reaction vessel, 0.5 g (4.15 mmol) of acetophenone, 250 mg (0.415 mmol) of [Ru(R,R)-Tsdpen (p-cymene)], and 42 mg of 2-propanol were added, followed by purging with nitrogen. In this solution, a reaction was allowed to proceed at room temperature for 2 hours.

The conversion to (R)-phenylethanol was 86%, and the optical purity was 91% ee.

Moreover, 67.3 mg (0.622 mmol) of α-phenylenediamine was added to the reaction solution, and the reaction solution was stirred. As a result, the color of the solution changed from reddish brown to purple. The solvent was removed by distillation under reduced pressure, and reslurring in heptane was conducted to remove acetophenone and phenylethanol. After, drying, mass spectrometry was conducted. The mass was 679.1438. From the mass spectrometry, the obtained compound was assumed to be Ru[(R,R)-Tsdpen](phenylenediamine)$_2$.

((R)-Phenethyl Alcohol Racemization Experiment)

The reaction shown below was conducted in the presence of Ru[(R,R)-Tsdpen](phenylenediamine)$_2$ in an amount of 0.5 equivalents to a substrate (phenylethanol having an optical purity of (R)-phenylethanol of 94.5% ee). In addition, the reaction shown below was conducted in the same manner in the presence of [Ru(R,R)-Tsdpen(p-cymene)] instead of Ru[(R,R)-Tsdpen](phenylenediamine)$_2$. Moreover, the reaction shown below was conducted in the same manner while 1.5 equivalents of α-phenylenediamine was added in addition to [Ru(R,R)-Tsdpen(p-cymene)].

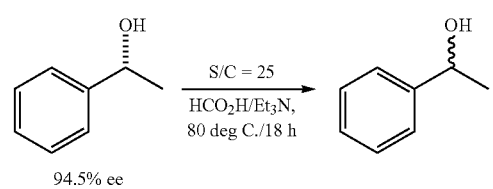

Table 1 shows the obtained results. From Table 1, it can be seen that no racemization proceeds in the presence of Ru[(R,R)-Tsdpen](phenylenediamine)$_2$ or in the presence of [Ru(R,R)-Tsdpen(p-cymene)] and α-phenylenediamine.

TABLE 1

| | Optical Purity |
|---|---|
| Ru[(R,R)-Tsdpen](phenylenediamine)$_2$ | 94.5% ee |
| [Ru(R,R)-Tsdpen(p-cymene)] | 75.3% ee |
| [Ru(R,R)-Tsdpen(p-cymene)] and α-phenylenediamine | 93.2% ee |

Reference Example 1: Asymmetric Hydrogen Transfer Reaction of Acetophenone

To a 200 ml reaction vessel, 10 g (8.32 mmol) of acetophenone, 1.06 g (1.6646 mmol) of [RuCl(S,S)-Tsdpen(p-cymene)], and 41.5 ml of formic acid/triethylamine (5/2 (volume ratio)) were added, followed by purging with nitrogen. This solution was stirred at 30° C. for 17 hours. Then, 45 ml of methylene chloride and 40 ml of water were added thereto, and the organic layer was separated. From the organic layer, methylene chloride was removed by distillation to obtain 13.5 g of an (S)-phenylethanol concentrate. This concentrate was stored at 5° C. for 4 days. The change in optical purity from the completion of the reaction was as follows.

TABLE 2

| Completion of reaction | Concentrate | 5° C., 4 days |
|---|---|---|
| 97.1% ee | 96.6% ee | 79.5% ee |

Comparative Example 1

One gram of the (S)-phenylethanol concentrate having an optical purity of 79.5% ee, obtained in Reference Example 1, and stored at 5° C. for 4 days was heated at 80° C. for 16 hours. As a result, the optical purity decreased to 13.6% ee.

Examples 2 to 5

Nitrogen-containing compounds were each added to 1 g (Ru: 0.123 mmol) of the (S)-phenylethanol concentrate having an optical purity of 79.5% ee, obtained in Reference Example 1, and stored at 5° C. for 4 days, and the mixtures were heated at 80° C. for 16 hours. The results were as shown in the following table.

TABLE 3

| Example | Additive | Equivalents | Optical purity |
|---|---|---|---|
| 2 | Triethylenetetramine | 3 | 79.5% ee |
| 3 | 3,4-Diaminobenzoic acid | 2 | 79.5% ee |
| 4 | Imidazole | 2 | 79.5% ee |
| 5 | Bipyridine | 2 | 71.4% ee |

Example 6: Synthesis of (R)-4-(1-Hydroxyethyl)benzonitrile

To a 200 mL four-necked flask, 15.0 g (103.3 mmol) of 4-acetylbenzonitrile, 30 ml of MeOH, and 126 mg (0.2 mmol) of [RuCl(R,R)-Tsdpen(p-cymene)] were added. While the temperature was kept at 15° C., 75 ml of formic acid/triethylamine (5/2 (volume ratio)) was added dropwise at 20° C. or below over 30 minutes. After the temperature was raised to 25° C., the mixture was stirred for 64 hours. After completion of the reaction, the mixture was cooled to 15° C. Then, 30 ml of water was added, and extraction was conducted with 90 ml of ethyl acetate, followed by washing with 30 ml of water twice. Subsequently, 75.5 mg (0.5 mmol) of triethylenetetramine was weighed in a 300 ml recovery flask, and the ethyl acetate extract solution was added to the recovery flask. Under reduced pressure, ethyl acetate was removed by distillation. The obtained liquid concentrate (14.4 g (95.9% ee)) was purified by distillation under reduced pressure (118 to 120° C./1 torr) to obtain 11.7 g of the desired (R)-4-(1-hydroxyethyl)benzonitrile (yield 76.9%).

The optical purity was 95.6% ee.

Comparative Example 2

The same procedures as in Example 6 were conducted, except that no triethylenetetramine was added. The optical purity of the distillate was 86.2% ee.

Reference Example 2: Asymmetric Hydrogen Transfer Reaction of Acetophenone

To a 200 ml reaction vessel, 10 g (8.30 mmol) of acetophenone, 1.00 g (1.5712 mmol) of [RuCl(S,S)-Tsdpen(p-cymene)], 300 ml of 2-propanol, and 300 mg (7.500 mmol) of sodium hydroxide were added, followed by purging with nitrogen. This solution was stirred at 40° C. for 22 hours, and then the solvent was removed by distillation to obtain 11.3 g of (S)-phenylethanol concentrate. The change in optical purity from the completion of the reaction was as follows.

TABLE 4

| Completion of reaction | Concentrate |
|---|---|
| 84.2% ee | 83.9% ee |

Comparative Example 2

One gram of the (S)-phenylethanol concentrate having an optical purity of 83.9% ee obtained in Reference Example 2 was heated at 80° C. for 17 hours. As a result, the optical purity decreased to 78.2% ee.

Examples 7 to 9

Nitrogen-containing compounds were each added to 1 g (Ru: 0.138 mmol) of a (S)-phenylethanol concentrate having an optical purity of 83.9% ee and obtained by the same procedures as in Reference Example 2, and the mixtures were heated at 80° C. for 17 hours. The results were as shown in the following Table.

TABLE 5

| Example | Additive | Equivalents | Optical purity |
|---|---|---|---|
| 7 | Diethylenetriamine | 2 | 83.6% ee |
| 8 | Imidazole | 2 | 83.8% ee |
| 9 | Bipyridine | 2 | 83.8% ee |

Reference Example 3: Racemization of Optically Active (R)-Phenylethanol

To a 200 ml reaction vessel, 100 mg (0.819 mmol) of (R)-phenylethanol (94.5% ee), 24.6 mg (0.041 mmol) of

[Ru(R,R)-Tsdpen(p-cymene)], and 2 ml of formic acid/triethylamine (5/2 (volume ratio)) were added, followed by purging with nitrogen. This solution was stirred at 80° C. for 17 hours. As a result, the optical purity was 55.4% ee.

Examples 10 to 15

The same procedures as in Reference Example 3 were conducted, except that nitrogen-containing compounds were added to reaction vessels. The results were as shown in the following Table.

TABLE 6

| Example | Additive | Equivalents | Optical purity |
|---------|----------|-------------|----------------|
| 10 | 2-Methylimidazole | 1.5 | 90.1% ee |
| 11 | 2-Methylimidazole | 3 | 93.7% ee |
| 12 | 1-Methylimidazole | 1.5 | 91.4% ee |
| 13 | 1,2,4-Thiazole | 1.5 | 93.3% ee |
| 14 | 2-Pyridinol | 1.5 | 92.0% ee |
| 15 | Pyrazole | 1.5 | 89.1% ee |

The invention claimed is:

1. A method for producing an optically active compound, comprising:
   conducting a reduction reaction of a compound in a solvent by using a ruthenium complex to form a reaction solution, wherein the compound has a group selected from the group consisting of a carbonyl group, a carbon-carbon double bond, an imino group and an ester group; wherein the reduction reaction is selected from the group consisting of asymmetric hydrogenation of the carbonyl group, asymmetric hydrogen transfer reaction of the carbonyl group, asymmetric hydrogenation of the carbon-carbon double bond, asymmetric hydrogenation of the imino group and ester reduction reaction of the ester group; and wherein the optically active compound is a product of the reduction reaction;
   adding a nitrogen-containing compound having two or more nitrogen atoms to the reaction solution after completion of the reduction reaction of the compound; and then
   performing a reaction solvent recovery and/or distillation.

2. The production method according to claim 1, wherein the nitrogen-containing compound is added in an amount of one or more equivalents relative to the ruthenium complex.

3. The production method according to claim 2, wherein the nitrogen-containing compound is an imidazole.

4. The production method according to claim 1, wherein the addition of the nitrogen-containing compound suppresses a decrease in optical purity of the optically active compound during the reaction solvent recovery and/or the distillation.

5. The production method according to claim 4, wherein the addition of the nitrogen-containing compound results in a reaction of the nitrogen-containing compound with the ruthenium complex to form a complex containing the nitrogen-containing compound, and thus suppresses the decrease in optical purity of the optically active compound.

* * * * *